(12) United States Patent
Takai et al.

(10) Patent No.: US 9,827,377 B2
(45) Date of Patent: Nov. 28, 2017

(54) SYRINGE AND SYRINGE GASKET

(71) Applicant: NIPRO CORPORATION, Osaka-shi, Osaka (JP)

(72) Inventors: Toshiyuki Takai, Osaka (JP); Motonori Nakamura, Osaka (JP)

(73) Assignee: NIPRO CORPORATION, Osaka-Shi (JP)

( * ) Notice: Subject to any disclaimer, the term of this patent is extended or adjusted under 35 U.S.C. 154(b) by 0 days.

(21) Appl. No.: 14/772,245

(22) PCT Filed: Mar. 4, 2014

(86) PCT No.: PCT/JP2014/055430
§ 371 (c)(1),
(2) Date: Sep. 2, 2015

(87) PCT Pub. No.: WO2014/136759
PCT Pub. Date: Sep. 12, 2014

(65) Prior Publication Data
US 2016/0022917 A1 Jan. 28, 2016

(30) Foreign Application Priority Data
Mar. 8, 2013 (JP) ................................. 2013-046883

(51) Int. Cl.
*A61M 5/315* (2006.01)
*A61M 5/31* (2006.01)

(52) U.S. Cl.
CPC .... *A61M 5/31513* (2013.01); *A61M 5/31515* (2013.01); *A61M 2005/3131* (2013.01)

(58) Field of Classification Search
CPC .......... A61M 5/31513; A61M 5/31515; A61M 5/3131; A61M 2005/3131; A61M 5/31511
See application file for complete search history.

(56) References Cited

U.S. PATENT DOCUMENTS 1,799,463 A    4/1931 Hein
6,331,174 B1 *  12/2001 Reinhard ................ A61M 5/28
                                          427/2.3
(Continued)

FOREIGN PATENT DOCUMENTS

EP    1 002 551 A2    5/2000
JP    2001-137338 A   5/2001
(Continued)

OTHER PUBLICATIONS

English translation of JP2010246842A, retrieved Oct. 26, 2016.*

*Primary Examiner* — Kami A Bosworth
*Assistant Examiner* — Alexandra Lalonde
(74) *Attorney, Agent, or Firm* — Birch, Stewart, Kolasch & Birch, LLP

(57) ABSTRACT

A gasket includes a flexible packing portion having a recess attached to a coupler of a plunger rod, and a core member harder than the packing portion. The recess has an internal circumferential surface with an internally threaded portion capable of being screwed on and thus engaging with an externally threaded portion provided on an external circumferential surface of the coupler. The core member has a helical shape defining the internal circumferential surface of the recess and the internally threaded portion provided on the internal circumferential surface. The packing portion defines a sliding surface brought into contact with an inner circumferential surface of a barrel, and the packing portion also covers an outer circumferential surface of the core member.

7 Claims, 3 Drawing Sheets

(56) References Cited

U.S. PATENT DOCUMENTS

| | | | | |
|---|---|---|---|---|
| 2007/0060896 A1* | 3/2007 | Miller | ............... | A61M 5/31511 604/222 |
| 2011/0178475 A1* | 7/2011 | Tanaka | ............... | A61M 5/31515 604/222 |

FOREIGN PATENT DOCUMENTS

| | | | |
|---|---|---|---|
| JP | 2001-190667 A | | 7/2001 |
| JP | 2002-210010 A | | 7/2002 |
| JP | 2003-235974 A | | 8/2003 |
| JP | 2004-8509 A | | 1/2004 |
| JP | 2008-307237 A | | 12/2008 |
| JP | 2010-246842 A | | 11/2010 |
| JP | 2010246842 A | * | 11/2010 |
| WO | WO 2005/099793 A1 | | 10/2005 |
| WO | WO 2007/027585 A2 | | 3/2007 |

\* cited by examiner

SYRINGE AND SYRINGE GASKET

CROSS-REFERENCE TO RELATED APPLICATIONS

This application is a National Stage Entry of PCT/JP2014/055430 filed on Mar. 4, 2014, which claims priority to Japanese Application No. 2013-046883 filed on Mar. 8, 2013, the entire contents of all the above applications are hereby incorporated by reference.

TECHNICAL FIELD

The present invention relates to a syringe gasket attached to an end of a plunger rod of a syringe slidably in a barrel of the syringe, and a syringe including the syringe gasket.

BACKGROUND ART

Syringe gaskets (hereinafter also simply referred to as a "gasket") are generally configured with natural rubber, isoprene rubber, styrene-butadiene rubber, butadiene rubber or other similar rubber materials contained as a major component, or with an elastomeric material as represented by a styrene butadiene copolymer contained as a major component.

When a rubber syringe gasket is compared with an elastomeric syringe gasket, the former normally exhibits a more excellent function in liquid tightness than the latter. However, some liquid medicines contain a component having nature to adsorb to rubber, and accordingly, when such a liquid medicine is used, the elastomeric syringe gasket is suitably used.

Note that typical syringe gaskets and syringes including the same are disclosed for example in Japanese Patent Laying-Open No. 2001-190667 (PTD 1) and Japanese Patent Laying-Open No. 2008-307237 (PTD 2).

SUMMARY OF INVENTION

Technical Problem

When a syringe gasket of elastomer, which is an excessively flexible material, experiences external force, however, it presents poor resilience in recovering to its original state and also requires a considerable period of time before it recovers its original state.

Accordingly, when a plunger rod and the gasket are screwed together and thus secured together, they cannot be secured together with sufficient strength, and the plunger rod escapes from the gasket. Furthermore, when a doctor or the like using a syringe with the gasket places and releases his/her fingers on its barrel at a location at which the gasket is located, a gap is instantaneously created between the barrel and the gasket and allows a liquid medicine in the syringe to leak therethrough.

While these problems remarkably arise for a syringe gasket of elastomer, the problems also arise for a syringe gasket of rubber correspondingly depending on its extent in flexibility.

The present invention has been made in view of such issues, and provides a syringe gasket being excellent in liquid tightness and capable of preventing the syringe gasket from escaping from a plunger rod.

Solution to Problem

A syringe according to the present invention includes: a barrel; a gasket disposed in the barrel slidably; and a plunger rod having the gasket attached thereto. The plunger rod has an end closer to the gasket and provided with a coupler having an external circumferential surface with an externally threaded portion. The gasket has an end closer to the plunger rod and provided with a recess having an internal circumferential surface with an internally threaded portion. The gasket is attached to the coupler by screwing the externally threaded portion on the internally threaded portion and thus engaging the externally threaded portion with the internally threaded portion. The gasket includes: a helical core member that defines the internal circumferential surface of the recess and the internally threaded portion provided on the internal circumferential surface; and a flexible packing portion that defines a sliding surface brought into contact with an inner circumferential surface of the barrel and also covers an outer circumferential surface of the core member. The core member is harder than the packing portion.

In the syringe according to the present invention, preferably, the core member is made of plastic, and in that case, preferably, the packing portion is made of one of elastomer and rubber.

In the syringe according to the present invention preferably the gasket is configured as an integrally molded product having the packing portion bonded to the core member.

In the syringe according to the present invention preferably the core member and the packing portion are formed by coinjection molding.

In the syringe according to the present invention preferably a space defined by the barrel and the gasket is filled with a liquid medicine.

A syringe gasket according to the present invention has a recess allowing the syringe gasket to be attached to a plunger rod of a syringe via a coupler provided at an end of the plunger rod so that the syringe gasket is slidable in a barrel of the syringe, and the syringe gasket includes: a flexible packing portion; and a core member harder than the packing portion. The recess has an internal circumferential surface with an internally threaded portion capable of being screwed on and thus engaging with an externally threaded portion provided on an external circumferential surface of the coupler. The core member has a helical shape defining the internal circumferential surface of the recess and the internally threaded portion provided on the internal circumferential surface. The packing portion defines a sliding surface brought into contact with an inner circumferential surface of the barrel and also covers an outer circumferential surface of the core member.

Advantageous Effect of Invention

The present invention can thus provide a syringe gasket being excellent in liquid tightness and capable of preventing the syringe gasket from escaping from a plunger rod.

DESCRIPTION OF EMBODIMENT

Hereinafter reference will be made to the drawings to describe one embodiment of the present invention. In describing the following embodiment(s), identical or corresponding components are identically denoted and will not be described repeatedly in detail.

Figure 1:
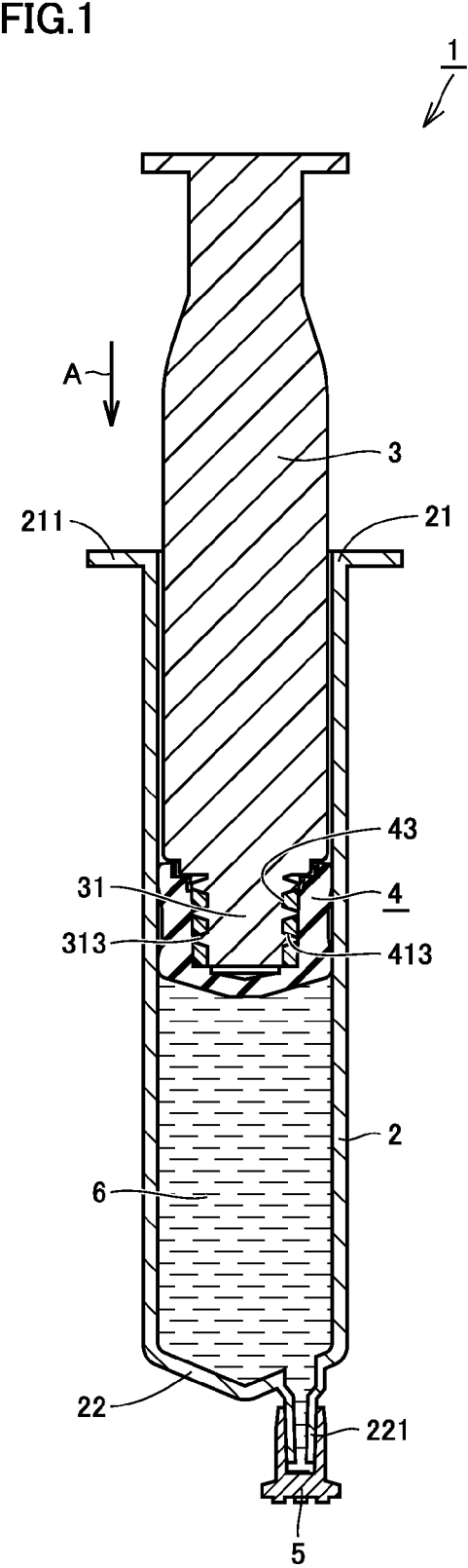
FIG. 1 is a cross section of a syringe in an embodiment of the present invention.

FIG. 1 is a cross section of a syringe in an embodiment of the present invention. Reference will first be made to FIG. 1 to describe a syringe 1 and a syringe gasket 4 in the present embodiment. Note that syringe 1 in the present embodiment is a so-called pre-filled syringe previously filled with a liquid medicine 6.

As shown in FIG. 1, syringe 1 includes a barrel 2, a plunger rod 3, gasket 4, a cap 5, and liquid medicine 6. Liquid medicine 6 is introduced in barrel 2 and tightly sealed from a space external thereto by barrel 2, gasket 4 and cap 5.

Barrel 2 is a bottomed, generally cylindrical member having one axial end or a proximal end 21 opened and the other axial end or a distal end 22 substantially closed and is configured as an injection-molded product made of resin. Barrel 2 has proximal end 21 with a flange 211 provided for allowing a user to hold barrel 2 for injection. Furthermore, barrel 2 has a bottom, which corresponds to distal end 22, with a needle attachment 221 allowing a needle to be attached thereto.

Needle attachment 221 has its tip opened and barrel 2 has an internal space communicating via needle attachment 221 with a space external to barrel 2. Cap 5 is attached to needle attachment 221 to allow barrel 2 to hold liquid medicine 6 therein tightly sealed at distal end 22 of syringe 1 from the external space.

Gasket 4 is a generally cylindrical member and is inserted in a space internal to barrel 2. Gasket 4 is disposed in barrel 2 slidably and has an outer circumferential surface partially serving as a sliding surface in contact with an inner circumferential surface of barrel 2 with appropriate pressure exerted thereto. An axial end of gasket 4 that is closer to distal end 22 of barrel 2 is in contact with liquid medicine 6 introduced in barrel 2. This allows barrel 2 to hold liquid medicine 6 therein tightly sealed by gasket 4 at a side closer to proximal end 21 of syringe 1 from the external space.

An axial end of gasket 4 that is closer to proximal end 21 of barrel 2 is provided with a recess 43 for allowing gasket 4 to be attached to plunger rod 3 at a coupler 31 described hereinafter. Recess 43 has an internal circumferential surface with an internally threaded portion 413. Gasket 4 will more specifically be described hereinafter.

Plunger rod 3 is a generally cylindrical member, and is configured for example as an injection-molded product made of resin. Plunger rod 3 has one axial end inserted into barrel 2 at proximal end 21 of barrel 2, and the other axial end projecting outside barrel 2.

Plunger rod 3 has one axial end with coupler 31, which is generally cylindrical and projects toward distal end 22 of barrel 2. Coupler 31 has an external circumferential surface with an externally threaded portion 313.

Coupler 31 is inserted in recess 43 of gasket 4. Note that gasket 4 is attached to coupler 31 by screwing externally threaded portion 313 that is provided on the external circumferential surface of coupler 31 on internally threaded portion 413 that is provided on the internal circumferential surface of recess 43, and thus engaging externally threaded portion 313 with internally threaded portion 413. This secures gasket 4 to one end of plunger rod 3.

When using syringe 1, a needle is attached to needle attachment 221 of barrel 2 such that the needle pierces cap 5, and plunger rod 3 is subsequently pushed in toward distal end 22 of barrel 2 (in a direction indicated in the figure by an arrow A). Gasket 4 will thus slide in barrel 2 toward distal end 22 while maintaining liquid tightness, and as gasket 4 slides, it applies pressure to deliver liquid medicine 6 to the needle via needle attachment 221.

Figure 2:
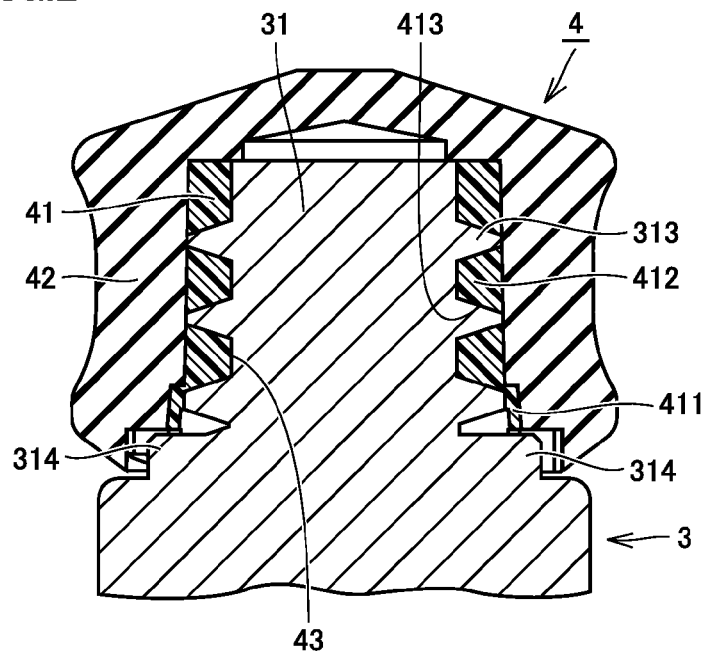
FIG. 2 is an enlarged cross section of a major portion of the syringe shown in FIG. 1.
Figure 3:
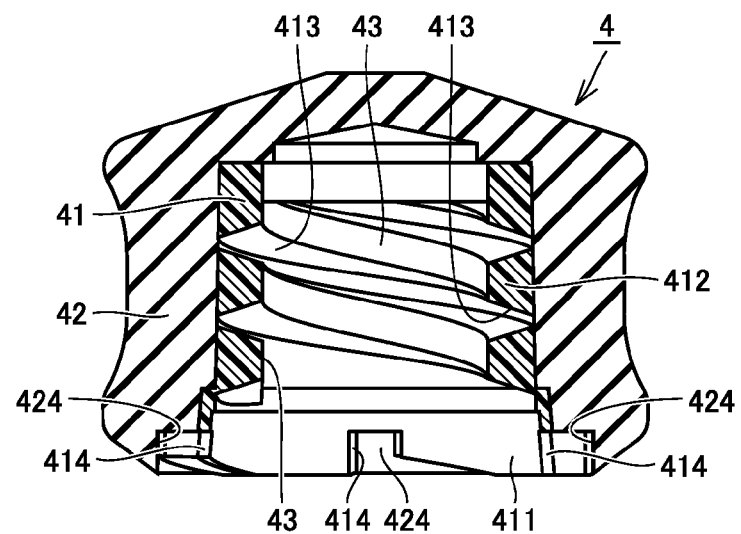
FIG. 3 is a cross section of a syringe gasket shown in FIG. 1.
Figure 4:
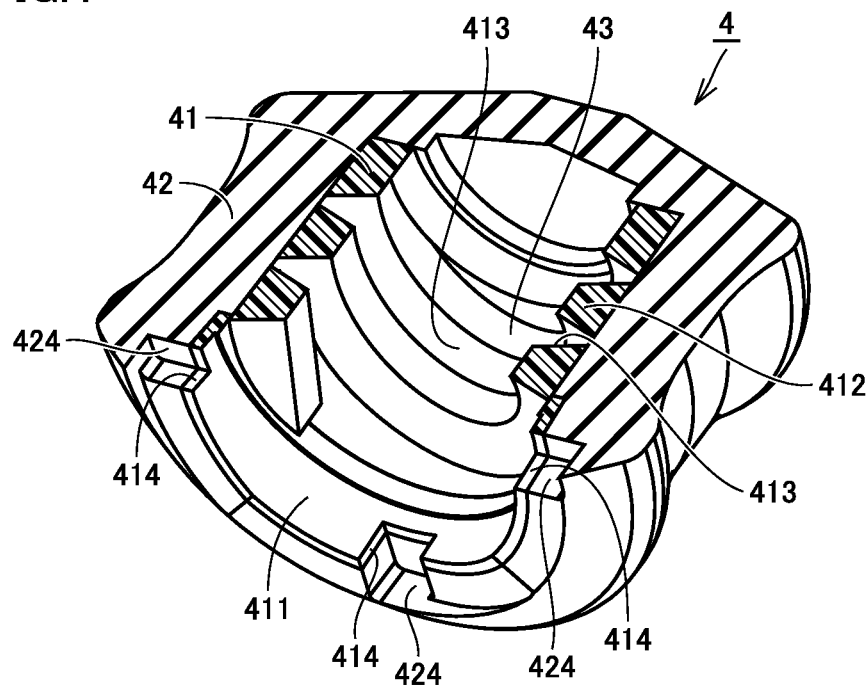
FIG. 4 is a partially cut-away perspective view of the syringe gasket shown in FIG. 1.
Figure 5:
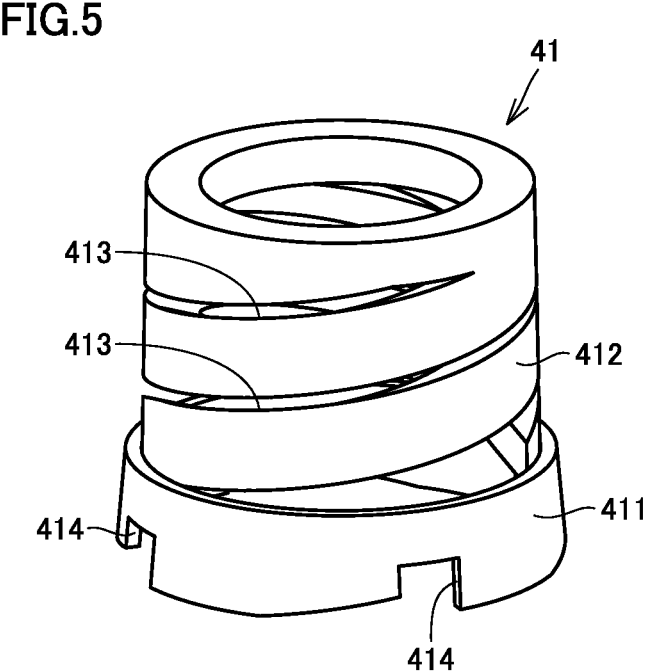
FIG. 5 is a perspective view of a core member of the syringe gasket shown in FIG. 1.

FIG. 2 is an enlarged cross section of a major portion of the syringe shown in FIG. 1, and FIGS. 3 and 4 are a cross section and a partially cut-away perspective view, respectively, of the syringe gasket shown in FIG. 1. Furthermore, FIG. 5 is a perspective view of a core member of the syringe gasket shown in FIG. 1. Hereinafter reference will be made to FIGS. 2-5 to describe syringe gasket 4 of the present embodiment more specifically in structure, and in what structure syringe gasket 4 is assembled to plunger rod 3 in syringe 1 in the present embodiment.

As shown in FIG. 2 to FIG. 4, gasket 4 includes a core member 41 and a packing portion 42. Recess 43 is defined by core member 41 and packing portion 42, and core member 41 defines an internal circumferential surface of recess 43 and packing portion 42 defines a bottom surface of recess 43.

Core member 41 mainly configures a portion of gasket 4 that is secured to plunger rod 3. Packing portion 42 mainly configures a portion of gasket 4 that tightly seals liquid medicine 6 inside barrel 2. Accordingly, core member 41 has its outer side covered with packing portion 42.

Core member 41 is a harder member than packing portion 42. Core member 41 can be made for example of plastic with polypropylene resin, polyethylene resin or the like as a major component. Note that when heat resistance is considered for a sterilization process, core member 41 is preferably made of polypropylene resin.

In contrast, packing portion 42 is a more flexible member than core member 41. Packing portion 42 can be made for example of rubber with natural rubber, isoprene rubber, styrene-butadiene rubber, butadiene rubber and/or the like as a major component, or of elastomer with a thermoplastic elastomer, such as represented by a styrene butadiene copolymer, as a major component. Note that if liquid medicine 6 contains a component having a nature to adsorb to rubber, packing portion 42 is preferably made of elastomer.

Preferably, gasket 4 is configured as an integrally molded product having packing portion 42 bonded to core member 41. Specifically, it is produced using a molding and welding technique using a die and implemented as insert molding, coinjection molding, or the like.

Insert molding is employed as follows: Core member 41 is previously formed of a plastic material by injection molding using a die. Core member 41 thus formed is then once completely released from the die. Core member 41 thus ejected is then set in another die as an insert and a melted rubber material or a melted elastomeric material is poured into a cavity of the die surrounding core member 41 that is set and the material is set to form packing portion 42 to thus obtain gasket 4.

Coinjection molding is employed as follows: Core member 41 is previously formed of a plastic material by injection molding using a die. Then, a portion of the die is separated to expose only a portion that serves as a surface of core member 41 that is bonded to packing portion 42 and the separated portion of the die is replaced with another die, which is set to cover the portion that will serve as the surface to be bonded to packing portion 42, and a melted rubber material or a melted elastomeric material is poured into a cavity of the die surrounding core member 41 and the material is set to form packing portion 42 to thus obtain gasket 4.

Using these techniques to configure gasket 4 as an integrally molded product allows core member 41 and packing portion 42 to have surfaces, respectively, firmly bonded together to allow gasket 4 to be handled as a single component. Note that when productivity is considered, coinjection molding is more suitable.

As shown in FIG. 2 to FIG. 5, core member 41 is helical in shape, and is as a whole generally cylindrical in shape including a collar 411 and a helical portion 412. Collar 411 is located at an end of gasket 4 that is closer to plunger rod 3, and helical portion 412 extends from collar 411 toward an end of gasket 4 that is located opposite to the end of gasket 4 that is closer to plunger rod 3.

Packing portion 42 is generally a bottomed cylinder in shape. Packing portion 42 has a cylindrical portion covering an outer circumferential surface of core member 41 (i.e., an outer circumferential surface of collar 411 and an outer circumferential surface of helical portion 412) and also defining an outer circumferential surface of gasket 4 including the sliding surface brought into contact with the inner circumferential surface of barrel 2. Furthermore, packing portion 42 has a bottom covering an end of core member 41 that is located opposite to an end thereof closer to plunger rod 3.

Note that core member 41 has helical portion 412 with a helically extending slit to define internally threaded portion 413. Internally threaded portion 413 is a portion screwed on and thus engaged with externally threaded portion 313 formed on the external circumferential surface of coupler 31 of plunger rod 3, as previously discussed, and is located on the internal circumferential surface of recess 43.

Furthermore, core member 41 has collar 411 with a plurality of notched engagement holes 414 provided circumferentially, and each portion of packing portion 42 that corresponds to engagement hole 414 is provided with an engagement groove 424. Engagement hole 414 and engagement groove 424 are portions that engage a projection 314 (see FIG. 2) formed at a foot of coupler 31 of plunger rod 3, and serve to stop rotation to prevent coupler 31 from being screwed off gasket 4.

Syringe 1 according to the present embodiment has gasket 4 configured of packing portion 42 that presents flexibility and core member 41 harder than packing portion 42, and gasket 4 has recess 43 allowing gasket 4 to be attached to plunger rod 3 via coupler 31, and internally threaded portion 413 provided on an internal circumferential surface of recess 43, with the internal circumferential surface and internally threaded portion 413 both defined by core member 41 that is helical in shape, and gasket 4 has a sliding surface in contact with an inner circumferential surface of barrel 2, that is defined by packing portion 42 that covers an outer circumferential surface of core member 41.

When syringe 1 according to the present embodiment is compared with a configuration having a gasket 4 entirely formed of a flexible material, the syringe 1 according to the present embodiment comprises a core member 41 which is harder than packing portion 42, and accordingly, can enhance packing portion 4 in force of repulsion, and if packing portion 42 is formed of a relatively soft material, the syringe 1 according to the present embodiment will nonetheless allow the gasket 4 to have enhanced resilience and also recover to its original state in a reduced period of time, and thus ensure high liquid tightness. In addition, the core member 41 that is hard allows the plunger rod 43 and the gasket 4 to be screwed together more firmly and thus secured together with significantly increased strength.

Syringe 1 and syringe gasket 4 according to the present embodiment can thus provide a syringe gasket excellent in liquid tightness and capable of preventing the syringe gasket from escaping from plunger rod 3, and a syringe including the syringe gasket.

Furthermore, a prefilled syringe or the like, such as presented by syringe 1 in the present embodiment having liquid medicine 6 previously introduced therein, has gasket 4 inserted into barrel 2 by employing a technique referred to as so-called sleeve knocking.

Sleeve knocking is done as follows: A jig in the form of a sleeve is prepared and a gasket is previously inserted therein in a compressed state. The jig with the gasket therein is then inserted into the barrel and a rod or the like is used to push the gasket in to a position to bring the gasket into contact with a liquid medicine, and thereafter the jig is alone extracted to leave the gasket in the barrel.

When sleeve knocking is employed to assemble a syringe, the gasket will be compressed more by the thickness of the jig in the form of the sleeve, and if the gasket has a hard portion, the gasket may have the hard portion deformed or crushed by the compressive force.

Syringe gasket 4 according to the above embodiment has a hard portion, or core member 41, that is helical in shape, i.e., a coiled spring in shape, and accordingly, will present springy resilience, and when this is compared with a gasket having core member 41 implemented as a cylindrical member or the like, the former presents a larger tolerance for deformation, breakage and the like than the latter.

The present embodiment provides a syringe 1 and a syringe gasket 4 that allows assembly of the gasket 4 into the barrel 2 via sleeve knocking with its core member 41, such that the gasket 4 is installed free from deformation, breakage and the like to produce syringes with good yield.

While the above embodiment of the present invention has been described for a gasket having a core member and a packing portion integrally molded to present an integrally molded product by way of example, the core member and the packing portion may be separately formed and subsequently combined together to configure the gasket.

Furthermore, while the above embodiment of the present invention has been described for a gasket and a plunger rod that are provided with a mechanism to stop rotation by way of example, this configuration is not essential.

Furthermore, while the above embodiment of the present invention has been described for a gasket including a core member having a helical portion and in addition thereto a collar by way of example, the collar is not essential, either.

Furthermore, while the above embodiment of the present invention has been described for a core member having an end opposite to a plunger rod, that is opened by way of example, the core member may have the end closed.

Furthermore, while the above embodiment of the present invention has described materials, shapes and the like for a variety of components, they are only illustrative and as a matter of course can be modified within a range allowed in light of the gist of the present invention.

In addition, while the above embodiment of the present invention has been described for a syringe and syringe gasket having the present invention applied thereto, that is implemented as a so-called prefilled syringe by way of example, the present invention is not limited thereto in application and is as a matter of course applicable to a syringe without any medicine previously introduced therein and a syringe gasket included in that syringe.

Thus the embodiment disclosed herein is illustrative and non-restrictive in any respect. The scope of the present invention is defined by the terms of the claims, and is intended to include any modifications within the meaning and scope equivalent to the terms of the claims.

REFERENCE SIGNS LIST

1: syringe; 2: barrel; 21: proximal end; 211: flange; 22: distal end; 221: needle attachment; 3: plunger rod; 31: coupler; 313: externally threaded portion; 314: projection; 4: (syringe) gasket; 41: core member; 411: collar; 412: helical portion; 413: internally threaded portion; 414: engagement hole; 42: packing portion; 424: engagement groove; 43: recess; 5: cap; 6: liquid medicine.

The invention claimed is:

1. A syringe comprising:
a barrel;
a gasket slidably disposed in said barrel; and
a plunger rod having said gasket attached thereto, said plunger rod having an end closer to said gasket and provided with a coupler having an external circumferential surface with an externally threaded portion,
said gasket having an end closer to said plunger rod and provided with a helical core member comprising a helically shaped internally threaded portion extending radially outward from an internal circumferential surface of the helical core member and the helically shaped internally threaded portion forming a helical slit in an outer circumferential surface of the helical core member,
said gasket being attached to said coupler by screwing said externally threaded portion on said internally threaded portion and thus engaging said externally threaded portion with said internally threaded portion,
said gasket further comprising a flexible packing portion that is configured to contact an inner circumferential surface of said barrel and to cover the outer circumferential surface of said helical core member, and said helical core member being harder than said flexible packing portion.

2. The syringe according to claim 1, wherein:
said helical core member is made of plastic; and said flexible packing portion is made of one of elastomer and rubber.

3. The syringe according to claim 1, wherein said gasket is configured as an integrally molded product having said flexible packing portion bonded to said helical core member.

4. The syringe according to claim 3, wherein said helical core member and said flexible packing portion are formed by coinjection molding.

5. The syringe according to claim 1, wherein a space defined by said barrel and said gasket is filled with a liquid medicine.

6. The syringe according to claim 1, further comprising a cap configured to be pierced by a needle,
said barrel further comprising a distal end provided with a needle attachment that is attached to said cap and configured to be attached to said needle.

7. A syringe gasket having a helically shaped internally threaded portion allowing the syringe gasket to be attached to a plunger rod of a syringe via a coupler provided at an end of said plunger rod so that the syringe gasket is slidable in a barrel of said syringe, the syringe gasket comprising:
a flexible packing portion; and
a helical core member harder than said flexible packing portion and provided with said helically shaped internally threaded portion,
said helical core member having an internal circumferential surface with said helically shaped internally threaded portion extending radially outward from the internal circumferential surface, the helically shaped internally threaded portion forming a helical slit in an outer circumferential surface of the helical core member and being capable of engaging with an externally threaded portion provided on an external circumferential surface of said coupler,
said helical core member having a helical shape defining said internal circumferential surface and said internally threaded portion, and
said flexible packing portion is configured to contact an inner circumferential surface of said barrel and to cover the outer circumferential surface of said helical core member.

* * * * *